(12) United States Patent
Shields et al.

(10) Patent No.: US 8,496,656 B2
(45) Date of Patent: *Jul. 30, 2013

(54) TISSUE SEALER WITH NON-CONDUCTIVE VARIABLE STOP MEMBERS AND METHOD OF SEALING TISSUE

(75) Inventors: Chelsea Shields, Portland, OR (US); Edward C. Meagher, Greenlawn, NY (US)

(73) Assignee: Covidien AG (CH)

( * ) Notice: Subject to any disclaimer, the term of this patent is extended or adjusted under 35 U.S.C. 154(b) by 1232 days.

This patent is subject to a terminal disclaimer.

(21) Appl. No.: 12/355,622

(22) Filed: Jan. 16, 2009

(65) Prior Publication Data

US 2009/0149853 A1 Jun. 11, 2009

Related U.S. Application Data

(63) Continuation of application No. 10/846,262, filed on May 14, 2004, now Pat. No. 7,491,201.

(60) Provisional application No. 60/470,632, filed on May 15, 2003.

(51) Int. Cl.
*A61B 18/14* (2006.01)
(52) U.S. Cl.
USPC .............................................. 606/51; 606/52
(58) Field of Classification Search
USPC ..................................................... 606/45–52
See application file for complete search history.

(56) References Cited

U.S. PATENT DOCUMENTS

| | | | |
|---|---|---|---|
| 1,586,645 | A | 6/1926 | Bierman |
| 1,813,902 | A | 7/1931 | Bovie |
| 1,822,330 | A | 9/1931 | Ainslie |
| 1,852,542 | A | 4/1932 | Sovatkin |
| 2,002,594 | A | 5/1935 | Wappler et al. |
| 2,011,169 | A | 8/1935 | Wappler |
| 2,031,682 | A | 2/1936 | Wappler et al. |
| 2,054,149 | A | 9/1936 | Wappler |
| 2,176,479 | A | 10/1939 | Willis |

(Continued)

FOREIGN PATENT DOCUMENTS

| | | |
|---|---|---|
| CA | 2104423 | 2/1994 |
| DE | 2415263 | 10/1975 |

(Continued)

OTHER PUBLICATIONS

Examiner's Report issued in Australia in Application No. 2009201853 dated Aug. 26, 2011.

(Continued)

*Primary Examiner* — Michael Peffley

(57) ABSTRACT

A bipolar forceps for sealing tissue includes an elongated shaft having opposing jaw members at a distal end thereof, each of the jaw members including an electrically conductive sealing surface. The jaw members are movable relative to one another from a first position wherein the jaw members are disposed in spaced relation relative to one another to a second position wherein the jaw members cooperate to grasp tissue therebetween. The bipolar forceps is connected to a source of electrical energy such that the jaw members are capable of conducting bipolar energy through tissue grasped therebetween to effect a seal. The distance between the electrically conductive sealing surfaces when tissue is held therebetween is adjusted based upon a sensed pre-surgical condition during activation.

14 Claims, 5 Drawing Sheets

U.S. PATENT DOCUMENTS

| | | |
|---|---|---|
| 2,305,156 A | 4/1941 | Grubel |
| 2,279,753 A | 4/1942 | Knopp |
| 2,327,353 A | 8/1943 | Karle |
| 2,632,661 A | 8/1948 | Cristofv |
| 2,668,538 A | 2/1954 | Baker |
| 2,796,065 A | 6/1957 | Kapp |
| 3,073,311 A | 1/1963 | Tibbs et al. |
| 3,459,187 A | 3/1967 | Pallotta |
| 3,372,288 A | 3/1968 | Wigington |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,801,766 A | 4/1974 | Morrison, Jr. |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,233,734 A | 11/1980 | Bies |
| 4,236,470 A | 12/1980 | Stenson |
| 4,300,564 A | 11/1981 | Furihata |
| 4,311,145 A | 1/1982 | Esty et al. |
| D263,020 S | 2/1982 | Rau, III |
| 4,370,980 A | 2/1983 | Lottick |
| 4,375,218 A * | 3/1983 | DiGeronimo ................ 606/52 |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,624,254 A | 11/1986 | McGarry et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| 371,664 A | 10/1987 | Brannan et al. |
| 4,733,662 A | 3/1988 | DeSatnick et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,938,761 A | 7/1990 | Ensslin |
| 4,947,009 A | 8/1990 | Osika et al. |
| 4,985,030 A | 1/1991 | Melzer et al. |
| 5,007,908 A | 4/1991 | Rydell |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,147,357 A | 9/1992 | Rose et al. |
| 5,151,102 A | 9/1992 | Kamiyama et al. |
| 5,151,978 A | 9/1992 | Bronikowski et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,313,027 A | 5/1994 | Inoue et al. |
| 5,314,445 A | 5/1994 | Degwitz et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,330,502 A | 7/1994 | Hassler et al. |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,350,391 A | 9/1994 | Iacovelli |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,374,277 A | 12/1994 | Hassler |
| 5,376,089 A | 12/1994 | Smith |
| 5,383,875 A | 1/1995 | Bays et al. |
| 5,383,897 A | 1/1995 | Wholey |
| 5,389,098 A | 2/1995 | Tsuruta et al. |
| 5,389,103 A | 2/1995 | Melzer et al. |
| 5,389,104 A | 2/1995 | Hahnen et al. |
| 5,391,166 A | 2/1995 | Eggers |
| 5,391,183 A | 2/1995 | Janzen et al. |

| | | | | | |
|---|---|---|---|---|---|
| 5,396,900 A | 3/1995 | Slater et al. | 5,597,107 A | 1/1997 | Knodel et al. |
| 5,403,312 A | 4/1995 | Yates et al. | 5,601,224 A | 2/1997 | Bishop et al. |
| 5,403,342 A | 4/1995 | Tovey et al. | 5,601,601 A | 2/1997 | Tal et al. |
| 5,405,344 A | 4/1995 | Williamson et al. | 5,601,641 A | 2/1997 | Stephens |
| 5,409,763 A | 4/1995 | Serizawa et al. | 5,603,711 A | 2/1997 | Parins et al. |
| 5,411,519 A | 5/1995 | Tovey et al. | 5,603,723 A | 2/1997 | Aranyi et al. |
| 5,411,520 A | 5/1995 | Nash et al. | 5,611,798 A | 3/1997 | Eggers |
| 5,413,571 A | 5/1995 | Katsaros et al. | 5,611,808 A | 3/1997 | Hossain et al. |
| 5,415,656 A | 5/1995 | Tihon et al. | 5,611,813 A | 3/1997 | Lichtman |
| 5,415,657 A | 5/1995 | Taymor-Luria | 5,620,415 A | 4/1997 | Lucey et al. |
| 5,422,567 A | 6/1995 | Matsunaga | 5,620,453 A | 4/1997 | Nallakrishnan |
| 5,423,810 A | 6/1995 | Goble et al. | 5,620,459 A | 4/1997 | Lichtman |
| 5,425,690 A | 6/1995 | Chang | 5,624,452 A | 4/1997 | Yates |
| 5,425,739 A | 6/1995 | Jessen | 5,626,578 A | 5/1997 | Tihon |
| 5,429,616 A | 7/1995 | Schaffer | 5,626,609 A | 5/1997 | Zvenyatsky et al. |
| 5,431,672 A | 7/1995 | Cote et al. | 5,630,833 A | 5/1997 | Katsaros et al. |
| 5,431,674 A | 7/1995 | Basile et al. | 5,637,110 A | 6/1997 | Pennybacker et al. |
| 5,437,292 A | 8/1995 | Kipshidze et al. | 5,638,003 A | 6/1997 | Hall |
| 5,438,302 A | 8/1995 | Goble | 5,643,294 A | 7/1997 | Tovey et al. |
| 5,439,478 A | 8/1995 | Palmer | 5,647,869 A | 7/1997 | Goble et al. |
| 5,441,517 A | 8/1995 | Kensey et al. | 5,647,871 A | 7/1997 | Levine et al. |
| 5,443,463 A | 8/1995 | Stern et al. | 5,649,959 A | 7/1997 | Hannam et al. |
| 5,443,464 A | 8/1995 | Russell et al. | 5,655,650 A | 8/1997 | Naitou |
| 5,443,480 A | 8/1995 | Jacobs et al. | 5,658,281 A | 8/1997 | Heard |
| 5,445,638 A | 8/1995 | Rydell et al. | D384,413 S | 9/1997 | Zlock et al. |
| 5,445,658 A | 8/1995 | Durrfeld et al. | 5,662,667 A | 9/1997 | Knodel |
| 5,449,480 A | 9/1995 | Kuriya et al. | 5,665,100 A | 9/1997 | Yoon |
| 5,451,224 A | 9/1995 | Goble et al. | 5,667,526 A | 9/1997 | Levin |
| 5,454,823 A | 10/1995 | Richardson et al. | 5,674,220 A | 10/1997 | Fox et al. |
| 5,454,827 A | 10/1995 | Aust et al. | 5,674,229 A | 10/1997 | Tovey et al. |
| 5,456,684 A | 10/1995 | Schmidt et al. | 5,681,282 A | 10/1997 | Eggers et al. |
| 5,458,598 A | 10/1995 | Feinberg et al. | 5,688,270 A | 11/1997 | Yates et al. |
| 5,460,629 A | 10/1995 | Shlain et al. | 5,690,652 A | 11/1997 | Wurster et al. |
| 5,461,765 A | 10/1995 | Linden et al. | 5,690,653 A | 11/1997 | Richardson et al. |
| 5,462,546 A | 10/1995 | Rydell | 5,693,051 A | 12/1997 | Schulze et al. |
| 5,472,442 A | 12/1995 | Klicek | 5,693,920 A | 12/1997 | Maeda |
| 5,472,443 A | 12/1995 | Cordis et al. | 5,695,522 A | 12/1997 | LeMaire, III et al. |
| 5,478,351 A | 12/1995 | Meade et al. | 5,700,261 A | 12/1997 | Brinkerhoff |
| 5,480,406 A | 1/1996 | Nolan et al. | 5,700,270 A | 12/1997 | Peyser et al. |
| 5,480,409 A | 1/1996 | Riza | 5,702,390 A | 12/1997 | Austin et al. |
| 5,484,436 A | 1/1996 | Eggers et al. | 5,707,369 A | 1/1998 | Vaitekunas et al. |
| 5,496,312 A | 3/1996 | Klicek | 5,709,680 A | 1/1998 | Yates et al. |
| 5,496,317 A | 3/1996 | Goble et al. | 5,716,366 A | 2/1998 | Yates |
| 5,496,347 A | 3/1996 | Hashiguchi et al. | 5,720,744 A | 2/1998 | Eggleston et al. |
| 5,499,997 A | 3/1996 | Sharpe et al. | 5,722,421 A | 3/1998 | Francese et al. |
| 5,509,922 A | 4/1996 | Aranyi et al. | 5,725,536 A | 3/1998 | Oberlin et al. |
| 5,512,721 A | 4/1996 | Young et al. | 5,727,428 A | 3/1998 | LeMaire, III et al. |
| 5,514,134 A | 5/1996 | Rydell et al. | 5,735,848 A | 4/1998 | Yates et al. |
| 5,527,313 A | 6/1996 | Scott et al. | 5,743,906 A | 4/1998 | Parins et al. |
| 5,528,833 A | 6/1996 | Sakuma | 5,752,973 A | 5/1998 | Kieturakis |
| 5,529,067 A | 6/1996 | Larsen et al. | 5,755,717 A | 5/1998 | Yates et al. |
| 5,531,744 A | 7/1996 | Nardella et al. | 5,759,188 A | 6/1998 | Yoon |
| 5,536,251 A | 7/1996 | Evard et al. | 5,766,130 A | 6/1998 | Selmonosky |
| 5,540,684 A | 7/1996 | Hassler, Jr. | 5,766,166 A | 6/1998 | Hooven |
| 5,540,685 A | 7/1996 | Parins et al. | 5,766,170 A | 6/1998 | Eggers |
| 5,540,706 A | 7/1996 | Aust et al. | 5,766,196 A | 6/1998 | Griffiths |
| 5,540,715 A | 7/1996 | Katsaros et al. | 5,769,849 A | 6/1998 | Eggers |
| 5,542,945 A | 8/1996 | Fritzsch | 5,772,655 A | 6/1998 | Bauer et al. |
| 5,558,671 A | 9/1996 | Yates | 5,772,670 A | 6/1998 | Brosa |
| 5,558,672 A | 9/1996 | Edwards et al. | 5,776,128 A | 7/1998 | Eggers |
| 5,562,619 A | 10/1996 | Mirarchi et al. | 5,776,130 A | 7/1998 | Buysse et al. |
| 5,562,699 A | 10/1996 | Heimberger et al. | 5,779,646 A | 7/1998 | Koblish et al. |
| 5,562,720 A | 10/1996 | Stern et al. | 5,779,701 A | 7/1998 | McBrayer et al. |
| 5,564,615 A | 10/1996 | Bishop et al. | H1745 H | 8/1998 | Paraschac |
| 5,569,241 A | 10/1996 | Edwards | 5,792,137 A | 8/1998 | Carr et al. |
| 5,569,243 A | 10/1996 | Kortenbach et al. | 5,792,165 A | 8/1998 | Klieman et al. |
| 5,571,100 A | 11/1996 | Goble et al. | 5,792,177 A | 8/1998 | Kaseda |
| 5,573,424 A | 11/1996 | Poppe | 5,797,537 A | 8/1998 | Oberlin et al. |
| 5,573,534 A | 11/1996 | Stone | 5,797,927 A | 8/1998 | Yoon |
| 5,573,535 A | 11/1996 | Viklund | 5,797,938 A | 8/1998 | Paraschac et al. |
| 5,575,799 A | 11/1996 | Bolanos et al. | 5,797,941 A | 8/1998 | Schulze et al. |
| 5,575,805 A | 11/1996 | Li | 5,797,958 A | 8/1998 | Yoon |
| 5,578,052 A | 11/1996 | Koros et al. | 5,800,449 A | 9/1998 | Wales |
| 5,579,781 A | 12/1996 | Cooke | 5,807,393 A | 9/1998 | Williamson, IV et al. |
| 5,582,611 A | 12/1996 | Tsukagoshi et al. | 5,810,764 A | 9/1998 | Eggers et al. |
| 5,582,617 A | 12/1996 | Klieman et al. | 5,810,805 A | 9/1998 | Sutcu et al. |
| 5,585,896 A | 12/1996 | Yamazaki et al. | 5,810,808 A | 9/1998 | Eggers |
| 5,590,570 A | 1/1997 | LeMaire, III et al. | 5,810,811 A | 9/1998 | Yates et al. |
| 5,591,181 A | 1/1997 | Stone et al. | 5,810,877 A | 9/1998 | Roth et al. |

| | | |
|---|---|---|
| 5,814,043 A | 9/1998 | Shapeton |
| 5,814,054 A | 9/1998 | Kortenbach et al. |
| 5,817,093 A | 10/1998 | Williamson, IV et al. |
| 5,817,119 A | 10/1998 | Klieman et al. |
| 5,820,630 A | 10/1998 | Lind |
| 5,824,978 A | 10/1998 | Karasik et al. |
| 5,827,271 A | 10/1998 | Buysse et al. |
| 5,827,279 A | 10/1998 | Hughett et al. |
| 5,827,281 A | 10/1998 | Levin |
| 5,827,323 A | 10/1998 | Klieman et al. |
| 5,827,548 A | 10/1998 | Lavallee et al. |
| 5,833,690 A | 11/1998 | Yates et al. |
| 5,843,080 A | 12/1998 | Fleenor et al. |
| 5,849,022 A | 12/1998 | Sakashita et al. |
| 5,853,412 A | 12/1998 | Mayenberger |
| 5,859,527 A | 1/1999 | Cook |
| 5,860,976 A | 1/1999 | Billings et al. |
| 5,876,401 A | 3/1999 | Schulze et al. |
| 5,876,412 A | 3/1999 | Piraka |
| 5,882,567 A | 3/1999 | Cavallaro et al. |
| 5,891,141 A | 4/1999 | Rydell |
| 5,891,142 A | 4/1999 | Eggers et al. |
| 5,893,863 A | 4/1999 | Yoon |
| 5,893,875 A | 4/1999 | O'Connor et al. |
| 5,893,877 A | 4/1999 | Gampp, Jr. et al. |
| 5,897,563 A | 4/1999 | Yoon et al. |
| 5,902,301 A | 5/1999 | Olig |
| 5,906,630 A | 5/1999 | Anderhub et al. |
| 5,908,420 A | 6/1999 | Parins et al. |
| 5,908,432 A | 6/1999 | Pan |
| 5,911,719 A | 6/1999 | Eggers |
| 5,913,874 A | 6/1999 | Berns et al. |
| 5,921,916 A | 7/1999 | Aeikens et al. |
| 5,921,984 A | 7/1999 | Sutcu et al. |
| 5,925,043 A | 7/1999 | Kumar et al. |
| 5,928,136 A | 7/1999 | Barry |
| 5,935,126 A | 8/1999 | Riza |
| 5,941,869 A | 8/1999 | Patterson et al. |
| 5,944,718 A | 8/1999 | Dafforn et al. |
| 5,951,546 A | 9/1999 | Lorentzen |
| 5,951,549 A | 9/1999 | Richardson et al. |
| 5,954,720 A | 9/1999 | Wilson et al. |
| 5,954,731 A | 9/1999 | Yoon |
| 5,954,733 A | 9/1999 | Yoon |
| 5,957,923 A | 9/1999 | Hahnen et al. |
| 5,957,937 A | 9/1999 | Yoon |
| 5,960,544 A | 10/1999 | Beyers |
| 5,961,514 A | 10/1999 | Long et al. |
| 5,964,758 A | 10/1999 | Dresden |
| 5,976,132 A | 11/1999 | Morris |
| 5,984,932 A | 11/1999 | Yoon |
| 5,984,938 A | 11/1999 | Yoon |
| 5,984,939 A | 11/1999 | Yoon |
| 5,989,277 A | 11/1999 | LeMaire, III et al. |
| 5,993,466 A | 11/1999 | Yoon |
| 5,993,467 A | 11/1999 | Yoon |
| 5,997,565 A | 12/1999 | Inoue |
| 6,004,332 A | 12/1999 | Yoon et al. |
| 6,004,335 A | 12/1999 | Vaitekunas et al. |
| 6,010,516 A | 1/2000 | Hulka et al. |
| 6,017,358 A | 1/2000 | Yoon et al. |
| 6,021,693 A | 2/2000 | Feng-Sing |
| 6,024,741 A | 2/2000 | Williamson et al. |
| 6,024,743 A | 2/2000 | Edwards |
| 6,024,744 A | 2/2000 | Kese et al. |
| 6,027,522 A | 2/2000 | Palmer |
| 6,030,384 A | 2/2000 | Nezhat |
| 6,033,399 A | 3/2000 | Gines |
| 6,039,733 A | 3/2000 | Buysse et al. |
| 6,041,679 A | 3/2000 | Slater et al. |
| 6,050,996 A * | 4/2000 | Schmaltz et al. ............... 606/51 |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,059,782 A | 5/2000 | Novak et al. |
| 6,066,139 A | 5/2000 | Ryan et al. |
| 6,074,386 A | 6/2000 | Goble et al. |
| 6,077,287 A | 6/2000 | Taylor et al. |
| 6,080,180 A | 6/2000 | Yoon et al. |
| RE36,795 E | 7/2000 | Rydell |
| 6,083,223 A | 7/2000 | Baker |
| 6,086,586 A | 7/2000 | Hooven |
| 6,086,601 A | 7/2000 | Yoon |
| 6,090,107 A | 7/2000 | Borgmeier et al. |
| 6,096,037 A | 8/2000 | Mulier et al. |
| 6,099,550 A | 8/2000 | Yoon |
| 6,102,909 A | 8/2000 | Chen et al. |
| 6,106,542 A | 8/2000 | Toybin et al. |
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| 6,122,549 A | 9/2000 | Sharkey et al. |
| 6,123,701 A | 9/2000 | Nezhat |
| H1904 H | 10/2000 | Yates et al. |
| 6,126,658 A | 10/2000 | Baker |
| 6,126,665 A | 10/2000 | Yoon |
| 6,139,563 A | 10/2000 | Cosgrove, III et al. |
| 6,143,005 A | 11/2000 | Yoon et al. |
| 6,152,923 A | 11/2000 | Ryan |
| 6,162,220 A | 12/2000 | Nezhat |
| 6,171,316 B1 | 1/2001 | Kovac et al. |
| 6,174,309 B1 | 1/2001 | Wrublewski et al. |
| 6,178,628 B1 | 1/2001 | Clemens et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,190,400 B1 | 2/2001 | VanDeMoer et al. |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,206,893 B1 | 3/2001 | Klein et al. |
| 6,214,028 B1 | 4/2001 | Yoon et al. |
| 6,217,602 B1 | 4/2001 | Redmon |
| 6,217,615 B1 | 4/2001 | Sioshansi et al. |
| 6,221,039 B1 | 4/2001 | Durgin et al. |
| 6,223,100 B1 | 4/2001 | Green |
| 6,224,593 B1 | 5/2001 | Ryan et al. |
| 6,224,614 B1 | 5/2001 | Yoon |
| 6,228,080 B1 | 5/2001 | Gines |
| 6,228,083 B1 | 5/2001 | Lands et al. |
| 6,248,124 B1 | 6/2001 | Pedros et al. |
| 6,248,944 B1 | 6/2001 | Ito |
| 6,261,307 B1 | 7/2001 | Yoon et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,298,550 B1 | 10/2001 | Kirwan |
| 6,302,424 B1 | 10/2001 | Gisinger et al. |
| 6,319,262 B1 | 11/2001 | Bates et al. |
| 6,319,451 B1 | 11/2001 | Brune |
| 6,322,561 B1 | 11/2001 | Eggers et al. |
| 6,322,580 B1 | 11/2001 | Kanner |
| 6,325,795 B1 | 12/2001 | Lindemann et al. |
| 6,334,860 B1 | 1/2002 | Dorn |
| 6,334,861 B1 | 1/2002 | Chandler et al. |
| 6,345,532 B1 | 2/2002 | Coudray et al. |
| 6,350,264 B1 | 2/2002 | Hooven |
| 6,352,536 B1 | 3/2002 | Buysse et al. |
| 6,358,249 B1 | 3/2002 | Chen et al. |
| 6,358,259 B1 | 3/2002 | Swain et al. |
| 6,358,268 B1 | 3/2002 | Hunt et al. |
| 6,364,879 B1 | 4/2002 | Chen et al. |
| D457,958 S | 5/2002 | Dycus et al. |
| D457,959 S | 5/2002 | Tetzlaff et al. |
| 6,387,094 B1 | 5/2002 | Eitenmuller |
| 6,391,035 B1 | 5/2002 | Appleby et al. |
| 702,472 A1 | 6/2002 | Pignolet |
| 6,398,779 B1 | 6/2002 | Buysse et al. |
| 6,402,747 B1 | 6/2002 | Lindemann et al. |

| Patent | Date | Inventor |
|---|---|---|
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,432,112 B2 | 8/2002 | Brock et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |
| 6,461,352 B2 | 10/2002 | Morgan et al. |
| 6,461,368 B2 | 10/2002 | Fogarty et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,485,489 B2 | 11/2002 | Teirstein et al. |
| 6,494,888 B1 | 12/2002 | Laufer et al. |
| 6,500,176 B1 | 12/2002 | Truckai et al. |
| 6,506,196 B1 | 1/2003 | Laufer |
| 6,508,815 B1 | 1/2003 | Strul et al. |
| 6,511,480 B1 | 1/2003 | Tetzlaff et al. |
| 6,514,215 B1 | 2/2003 | Ouchi |
| 6,514,252 B2 | 2/2003 | Nezhat et al. |
| 6,517,539 B1 | 2/2003 | Smith et al. |
| 6,527,771 B1 | 3/2003 | Weadock et al. |
| 6,533,784 B2 | 3/2003 | Truckai et al. |
| 6,545,239 B2 | 4/2003 | Spedale et al. |
| 728,883 A1 | 5/2003 | Downes |
| 6,558,385 B1 | 5/2003 | McClurken et al. |
| 6,562,037 B2 * | 5/2003 | Paton et al. .................. 606/51 |
| 6,569,105 B1 | 5/2003 | Kortenbach et al. |
| 6,582,450 B2 | 6/2003 | Ouchi |
| 6,585,735 B1 | 7/2003 | Frazier et al. |
| 6,602,252 B2 | 8/2003 | Mollenauer |
| 6,605,790 B2 | 8/2003 | Yoshida |
| 6,616,658 B2 | 9/2003 | Ineson |
| 6,616,661 B2 | 9/2003 | Wellman et al. |
| 6,620,161 B2 | 9/2003 | Schulze et al. |
| 6,620,184 B2 | 9/2003 | De Laforcade et al. |
| 6,626,901 B1 | 9/2003 | Treat et al. |
| 6,638,287 B2 | 10/2003 | Danitz et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,175 B2 | 12/2003 | Francischelli et al. |
| 6,656,177 B2 | 12/2003 | Truckai et al. |
| 6,660,072 B2 | 12/2003 | Chatterjee |
| 6,663,639 B1 | 12/2003 | Laufer et al. |
| 6,663,641 B1 | 12/2003 | Kovac et al. |
| 6,666,854 B1 | 12/2003 | Lange |
| 6,669,696 B2 | 12/2003 | Bacher et al. |
| 6,673,092 B1 | 1/2004 | Bacher |
| 6,676,660 B2 | 1/2004 | Wampler et al. |
| 6,676,676 B2 | 1/2004 | Danitz et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,693,246 B1 | 2/2004 | Rudolph et al. |
| 6,695,840 B2 | 2/2004 | Schulze |
| 6,702,810 B2 | 3/2004 | McClurken et al. |
| 6,723,092 B2 | 4/2004 | Brown et al. |
| 6,726,068 B2 | 4/2004 | Miller |
| 6,726,686 B2 | 4/2004 | Buysse et al. |
| 6,726,694 B2 | 4/2004 | Blatter et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,743,239 B1 | 6/2004 | Kuehn et al. |
| 6,743,240 B2 | 6/2004 | Smith et al. |
| 6,755,843 B2 | 6/2004 | Chung et al. |
| 6,756,553 B1 | 6/2004 | Yamaguchi et al. |
| 6,757,977 B2 | 7/2004 | Dambal et al. |
| D493,888 S | 8/2004 | Reschke |
| 6,770,072 B1 | 8/2004 | Truckai et al. |
| 6,773,409 B2 | 8/2004 | Truckai et al. |
| 6,773,432 B1 | 8/2004 | Clayman et al. |
| 6,773,434 B2 | 8/2004 | Ciarrocca |
| 6,773,441 B1 | 8/2004 | Laufer et al. |
| 6,775,575 B2 | 8/2004 | Bommannan et al. |
| 6,776,780 B2 | 8/2004 | Mulier et al. |
| 6,786,905 B2 | 9/2004 | Swanson et al. |
| 6,790,217 B2 | 9/2004 | Schulze et al. |
| 6,796,981 B2 | 9/2004 | Wham et al. |
| D496,997 S | 10/2004 | Dycus et al. |
| 6,800,825 B1 | 10/2004 | Sasaki et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,821,285 B2 | 11/2004 | Laufer et al. |
| 6,835,200 B2 | 12/2004 | Laufer et al. |
| 6,857,357 B2 | 2/2005 | Fujii |
| 6,860,880 B2 | 3/2005 | Treat et al. |
| 6,887,240 B2 | 5/2005 | Lands et al. |
| 6,889,116 B2 | 5/2005 | Jinno |
| 6,914,201 B2 | 7/2005 | Van Vooren et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| D509,297 S | 9/2005 | Wells |
| 6,942,662 B2 | 9/2005 | Goble et al. |
| 6,943,311 B2 | 9/2005 | Miyako |
| 6,953,430 B2 | 10/2005 | Kodooka |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,972,017 B2 | 12/2005 | Smith et al. |
| 6,977,495 B2 | 12/2005 | Donofrio |
| 6,979,786 B2 | 12/2005 | Aukland et al. |
| 6,981,628 B2 | 1/2006 | Wales |
| 6,987,244 B2 | 1/2006 | Bauer |
| 6,994,707 B2 | 2/2006 | Ellman et al. |
| 6,994,709 B2 | 2/2006 | Iida |
| 6,997,931 B2 | 2/2006 | Sauer et al. |
| 7,001,381 B2 | 2/2006 | Harano et al. |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,489 B2 | 5/2006 | Griego et al. |
| 7,052,496 B2 | 5/2006 | Yamauchi |
| 7,063,715 B2 | 6/2006 | Onuki et al. |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,051 B2 | 8/2006 | Bourne et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,107,124 B2 | 9/2006 | Green |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| D533,942 S | 12/2006 | Kerr et al. |

| | | | | | | |
|---|---|---|---|---|---|---|
| 7,145,757 | B2 | 12/2006 | Shea et al. | 2003/0018332 A1 | 1/2003 | Schmaltz et al. |
| 7,147,638 | B2 | 12/2006 | Chapman et al. | 2003/0069570 A1 | 4/2003 | Witzel et al. |
| 7,150,097 | B2 | 12/2006 | Sremcich et al. | 2003/0109875 A1 | 6/2003 | Tetzlaff et al. |
| 7,150,749 | B2 | 12/2006 | Dycus et al. | 2003/0114851 A1 | 6/2003 | Truckai et al. |
| 7,153,314 | B2 | 12/2006 | Laufer et al. | 2003/0139741 A1 | 7/2003 | Goble et al. |
| D535,027 | S | 1/2007 | James et al. | 2003/0158548 A1 | 8/2003 | Phan et al. |
| 7,156,842 | B2 | 1/2007 | Sartor et al. | 2003/0158549 A1 | 8/2003 | Swanson |
| 7,156,846 | B2 | 1/2007 | Dycus et al. | 2003/0171747 A1 | 9/2003 | Kanehira et al. |
| 7,160,298 | B2 | 1/2007 | Lawes et al. | 2003/0181910 A1 | 9/2003 | Dycus et al. |
| 7,160,299 | B2 | 1/2007 | Baily | 2003/0216732 A1 | 11/2003 | Truckai et al. |
| 7,169,146 | B2 | 1/2007 | Truckai et al. | 2003/0229344 A1 | 12/2003 | Dycus et al. |
| 7,179,255 | B2 | 2/2007 | Lettice et al. | 2003/0236325 A1 | 12/2003 | Bonora |
| 7,179,258 | B2 | 2/2007 | Buysse et al. | 2003/0236518 A1 | 12/2003 | Marchitto et al. |
| 7,195,631 | B2 | 3/2007 | Dumbauld | 2004/0030330 A1 | 2/2004 | Brassell et al. |
| D541,418 | S | 4/2007 | Schechter et al. | 2004/0064151 A1 | 4/2004 | Mollenauer |
| 7,207,990 | B2 | 4/2007 | Lands et al. | 2004/0073238 A1 | 4/2004 | Makower |
| D541,938 | S | 5/2007 | Kerr et al | 2004/0073256 A1 | 4/2004 | Marchitto et al. |
| 7,223,264 | B2 | 5/2007 | Daniel et al. | 2004/0115296 A1 | 6/2004 | Duffin |
| 7,223,265 | B2 | 5/2007 | Keppel | 2004/0143263 A1 | 7/2004 | Schechter et al. |
| 7,232,440 | B2 | 6/2007 | Dumbauld et al. | 2004/0148035 A1 | 7/2004 | Barrett et al. |
| 7,241,288 | B2 | 7/2007 | Braun | 2004/0162557 A1 | 8/2004 | Tetzlaff et al. |
| 7,241,296 | B2 | 7/2007 | Buysse et al. | 2004/0199181 A1 | 10/2004 | Knodel et al. |
| 7,244,257 | B2 | 7/2007 | Podjahsky et al. | 2004/0210282 A1 | 10/2004 | Flock et al. |
| 7,246,734 | B2 | 7/2007 | Shelto, IV | 2004/0224590 A1 | 11/2004 | Rawa et al. |
| 7,248,944 | B2 | 7/2007 | Green | 2004/0236326 A1 | 11/2004 | Schulze et al. |
| 7,252,667 | B2 | 8/2007 | Moses et al. | 2004/0249374 A1 | 12/2004 | Tetzlaff et al. |
| 7,255,697 | B2 | 8/2007 | Dycus et al. | 2004/0260281 A1 | 12/2004 | Baxter, III et al. |
| 7,267,677 | B2 | 9/2007 | Johnson et al. | 2005/0004564 A1 | 1/2005 | Wham et al. |
| 7,270,660 | B2 | 9/2007 | Ryan | 2005/0004569 A1 | 1/2005 | Witt et al. |
| 7,270,664 | B2 | 9/2007 | Johnson et al. | 2005/0033278 A1 | 2/2005 | McClurken et al. |
| 7,276,068 | B2 | 10/2007 | Johnson et al. | 2005/0059934 A1 | 3/2005 | Wenchell et al. |
| 7,300,435 | B2 | 11/2007 | Wham et al. | 2005/0096645 A1 | 5/2005 | Wellman et al. |
| 7,303,557 | B2 | 12/2007 | Wham et al. | 2005/0101952 A1 | 5/2005 | Lands et al. |
| 7,311,709 | B2 | 12/2007 | Truckai et al. | 2005/0149017 A1 | 7/2005 | Dycus |
| 7,314,471 | B2 | 1/2008 | Holman | 2005/0154387 A1 | 7/2005 | Moses et al. |
| 7,318,823 | B2 | 1/2008 | Sharps et al. | 2005/0187547 A1 | 8/2005 | Sugi |
| 7,329,256 | B2 | 2/2008 | Johnson et al. | 2005/0197659 A1 | 9/2005 | Bahney |
| 7,329,257 | B2 | 2/2008 | Kanehira et al. | 2005/0203504 A1 | 9/2005 | Wham et al. |
| D564,662 | S | 3/2008 | Moses et al. | 2006/0052778 A1 | 3/2006 | Chapman et al. |
| 7,338,526 | B2 | 3/2008 | Steinberg | 2006/0052779 A1 | 3/2006 | Hammill |
| 7,342,754 | B2 | 3/2008 | Fitzgerald et al. | 2006/0064086 A1 | 3/2006 | Odom |
| 7,344,268 | B2 | 3/2008 | Jhigamian | 2006/0079888 A1 | 4/2006 | Mulier et al. |
| D567,943 | S | 4/2008 | Moses et al. | 2006/0079890 A1 | 4/2006 | Guerra |
| 7,367,976 | B2 | 5/2008 | Lawes et al. | 2006/0079891 A1 | 4/2006 | Arts et al. |
| 7,377,920 | B2 | 5/2008 | Buysse et al. | 2006/0079933 A1 | 4/2006 | Hushka et al. |
| 7,384,420 | B2 | 6/2008 | Dycus et al. | 2006/0084973 A1 | 4/2006 | Hushka |
| 7,384,421 | B2 | 6/2008 | Hushka | 2006/0089670 A1 | 4/2006 | Hushka |
| 7,396,336 | B2 | 7/2008 | Orszulak et al. | 2006/0116675 A1 | 6/2006 | McClurken et al. |
| D575,395 | S | 8/2008 | Hushka | 2006/0129146 A1 | 6/2006 | Dycus et al. |
| D575,401 | S | 8/2008 | Hixson et al. | 2006/0167450 A1 | 7/2006 | Johnson et al. |
| 7,435,249 | B2 | 10/2008 | Buysse et al. | 2006/0167452 A1 | 7/2006 | Moses et al. |
| 7,442,193 | B2 | 10/2008 | Shields et al. | 2006/0173452 A1 | 8/2006 | Buysse et al. |
| 7,442,194 | B2 | 10/2008 | Dumbauld et al. | 2006/0190035 A1 | 8/2006 | Hushka et al. |
| 7,445,621 | B2 | 11/2008 | Dumbauld et al. | 2006/0217709 A1 | 9/2006 | Couture et al. |
| 7,458,972 | B2 | 12/2008 | Keppel | 2006/0229666 A1 | 10/2006 | Suzuki et al. |
| 7,473,253 | B2 | 1/2009 | Dycus et al. | 2006/0253126 A1 | 11/2006 | Bjerken et al. |
| 7,481,810 | B2 | 1/2009 | Dumbauld et al. | 2006/0259036 A1 | 11/2006 | Tetzlaff et al. |
| 7,487,780 | B2 | 2/2009 | Hooven | 2006/0264922 A1 | 11/2006 | Sartor et al. |
| 7,491,201 | B2 | 2/2009 | Shields et al. | 2006/0264931 A1 | 11/2006 | Chapman et al. |
| 7,491,202 | B2 | 2/2009 | Odom et al. | 2006/0283093 A1 | 12/2006 | Petrovic et al. |
| 7,500,975 | B2 | 3/2009 | Cunningham et al. | 2006/0287641 A1 | 12/2006 | Perlin |
| 7,510,556 | B2 | 3/2009 | Nguyen et al. | 2007/0016182 A1 | 1/2007 | Lipson et al. |
| 7,513,898 | B2 | 4/2009 | Johnson et al. | 2007/0016187 A1 | 1/2007 | Weinberg et al. |
| 7,540,872 | B2 | 6/2009 | Schechter et al. | 2007/0043352 A1 | 2/2007 | Garrison et al. |
| 7,549,995 | B2 | 6/2009 | Schultz | 2007/0043353 A1 | 2/2007 | Dycus et al. |
| 7,553,312 | B2 | 6/2009 | Tetzlaff et al. | 2007/0060919 A1 | 3/2007 | Isaacson et al. |
| 8,016,827 | B2 | 9/2011 | Chojin | 2007/0062017 A1 | 3/2007 | Dycus et al. |
| 8,114,122 | B2 | 2/2012 | Nau, Jr. | 2007/0074807 A1 | 4/2007 | Guerra |
| 8,142,473 | B2 | 3/2012 | Cunningham | 2007/0078456 A1 | 4/2007 | Dumbauld et al. |
| 8,162,973 | B2 | 4/2012 | Cunningham | 2007/0078458 A1 | 4/2007 | Dumbauld et al. |
| 8,197,479 | B2 | 6/2012 | Olson et al. | 2007/0078459 A1 | 4/2007 | Johnson et al. |
| 8,226,650 | B2 | 7/2012 | Kerr | 2007/0088356 A1 | 4/2007 | Moses et al. |
| 8,251,994 | B2 | 8/2012 | McKenna et al. | 2007/0106295 A1 | 5/2007 | Garrison et al. |
| 8,257,387 | B2 | 9/2012 | Cunningham | 2007/0106297 A1 | 5/2007 | Dumbauld et al. |
| 8,282,634 | B2 | 10/2012 | Cunningham et al. | 2007/0118111 A1 | 5/2007 | Weinberg |
| 2002/0107517 | A1 | 8/2002 | Witt et al. | 2007/0118115 A1 | 5/2007 | Artale et al. |
| 2002/0111624 | A1 | 8/2002 | Witt et al. | 2007/0142833 A1 | 6/2007 | Dycus et al. |
| 2003/0014052 | A1 | 1/2003 | Buysse et al. | 2007/0142834 A1 | 6/2007 | Dumbauld |
| 2003/0014053 | A1 | 1/2003 | Nguyen et al. | 2007/0156139 A1 | 7/2007 | Schechter et al. |

| | | | | | | |
|---|---|---|---|---|---|---|
| 2007/0156140 A1 | 7/2007 | Baily | | 2010/0094287 A1 | 4/2010 | Cunningham et al. |
| 2007/0173811 A1 | 7/2007 | Couture et al. | | 2010/0100122 A1 | 4/2010 | Hinton |
| 2007/0173814 A1 | 7/2007 | Hixson et al. | | 2010/0179545 A1 | 7/2010 | Twomey et al. |
| 2007/0179499 A1 | 8/2007 | Garrison | | 2010/0179546 A1 | 7/2010 | Cunningham |
| 2007/0198011 A1 | 8/2007 | Sugita | | | | |
| 2007/0213712 A1 | 9/2007 | Buysse et al. | | FOREIGN PATENT DOCUMENTS | | |
| 2007/0255279 A1 | 11/2007 | Buysse et al. | | | | |
| 2007/0260235 A1 | 11/2007 | Podhajsky | | DE | 2514501 | 10/1976 |
| 2007/0260238 A1 | 11/2007 | Guerra | | DE | 2627679 | 1/1977 |
| 2007/0260241 A1 | 11/2007 | Dalla Betta et al. | | DE | 3612646 | 4/1987 |
| 2007/0260242 A1 | 11/2007 | Dycus et al. | | DE | 8712328 | 3/1988 |
| 2007/0265616 A1 | 11/2007 | Couture et al. | | DE | 4303882 | 8/1994 |
| 2008/0004616 A1 | 1/2008 | Patrick | | DE | 4403252 | 8/1995 |
| 2008/0009860 A1 | 1/2008 | Odom | | DE | 19515914 | 7/1996 |
| 2008/0015575 A1 | 1/2008 | Odom et al. | | DE | 29616210 | 1/1997 |
| 2008/0021450 A1 | 1/2008 | Couture | | DE | 19608716 | 4/1997 |
| 2008/0033428 A1 | 2/2008 | Artale et al. | | DE | 19751106 | 5/1998 |
| 2008/0039835 A1 | 2/2008 | Johnson et al. | | DE | 19751108 | 5/1999 |
| 2008/0039836 A1 | 2/2008 | Odom et al. | | DE | 19738457 | 1/2009 |
| 2008/0045947 A1 | 2/2008 | Johnson et al. | | EP | 0364216 | 4/1990 |
| 2008/0058802 A1 | 3/2008 | Couture et al. | | EP | 0467501 | 1/1992 |
| 2008/0082100 A1 | 4/2008 | Orton et al. | | EP | 0518230 | 12/1992 |
| 2008/0091189 A1 | 4/2008 | Carlton | | EP | 0541930 | 5/1993 |
| 2008/0195093 A1 | 8/2008 | Couture et al. | | EP | 0572131 | 12/1993 |
| 2008/0215051 A1 | 9/2008 | Buysse et al. | | EP | 0584787 | 3/1994 |
| 2008/0243120 A1 | 10/2008 | Lawes et al. | | EP | 0589453 | 3/1994 |
| 2008/0249527 A1 | 10/2008 | Couture | | EP | 0589555 | 3/1994 |
| 2008/0312653 A1 | 12/2008 | Arts et al. | | EP | 0623316 | 11/1994 |
| 2008/0319442 A1 | 12/2008 | Unger et al. | | EP | 0624348 | 11/1994 |
| 2009/0012520 A1 | 1/2009 | Hixson et al. | | EP | 0650701 | 5/1995 |
| 2009/0018535 A1 | 1/2009 | Schechter et al. | | EP | 0694290 | 3/1996 |
| 2009/0024126 A1 | 1/2009 | Artale et al. | | EP | 0717966 | 6/1996 |
| 2009/0043304 A1 | 2/2009 | Tetzlaff et al. | | EP | 0754437 | 3/1997 |
| 2009/0048596 A1 | 2/2009 | Shields et al. | | EP | 0517243 | 9/1997 |
| 2009/0062794 A1 | 3/2009 | Buysse et al. | | EP | 0853922 | 7/1998 |
| 2009/0082766 A1 | 3/2009 | Unger et al. | | EP | 0875209 | 11/1998 |
| 2009/0082767 A1 | 3/2009 | Unger et al. | | EP | 0878169 | 11/1998 |
| 2009/0082769 A1 | 3/2009 | Unger et al. | | EP | 0887046 | 1/1999 |
| 2009/0088738 A1 | 4/2009 | Guerra et al. | | EP | 0923907 | 6/1999 |
| 2009/0088739 A1 | 4/2009 | Hushka et al. | | EP | 0986990 | 3/2000 |
| 2009/0088740 A1 | 4/2009 | Guerra et al. | | EP | 1034747 | 9/2000 |
| 2009/0088741 A1 | 4/2009 | Hushka et al. | | EP | 1034748 | 9/2000 |
| 2009/0088744 A1 | 4/2009 | Townsend | | EP | 1025807 | 10/2000 |
| 2009/0088745 A1 | 4/2009 | Hushka et al. | | EP | 1034746 | 10/2000 |
| 2009/0088746 A1 | 4/2009 | Hushka et al. | | EP | 1050278 | 11/2000 |
| 2009/0088747 A1 | 4/2009 | Hushka et al. | | EP | 1053719 | 11/2000 |
| 2009/0088748 A1 | 4/2009 | Guerra et al. | | EP | 1053720 | 11/2000 |
| 2009/0088749 A1 | 4/2009 | Hushka et al. | | EP | 1055399 | 11/2000 |
| 2009/0088750 A1 | 4/2009 | Hushka et al. | | EP | 1055400 | 11/2000 |
| 2009/0112206 A1 | 4/2009 | Dumbauld et al. | | EP | 1080694 | 3/2001 |
| 2009/0131934 A1 | 5/2009 | Odom et al. | | EP | 1082944 | 3/2001 |
| 2009/0149853 A1 | 6/2009 | Shields et al. | | EP | 1159926 | 12/2001 |
| 2009/0149854 A1 | 6/2009 | Cunningham et al. | | EP | 1177771 | 2/2002 |
| 2009/0171350 A1 | 7/2009 | Dycus et al. | | EP | 1301135 | 4/2003 |
| 2009/0171353 A1 | 7/2009 | Johnson et al. | | EP | 1330991 | 7/2003 |
| 2009/0182327 A1 | 7/2009 | Unger | | EP | 1486177 | 6/2004 |
| 2009/0187188 A1 | 7/2009 | Guerra et al. | | EP | 1472984 | 11/2004 |
| 2009/0198233 A1 | 8/2009 | Chojin | | EP | 0774232 | 1/2005 |
| 2009/0209957 A1 | 8/2009 | Schmaltz et al. | | EP | 1527747 | 5/2005 |
| 2009/0209960 A1 | 8/2009 | Chojin | | EP | 1530952 | 5/2005 |
| 2009/0234354 A1 | 9/2009 | Johnson et al. | | EP | 1532932 | 5/2005 |
| 2009/0248021 A1 | 10/2009 | McKenna | | EP | 1535581 | 6/2005 |
| 2010/0016857 A1 | 1/2010 | McKenna et al. | | EP | 1609430 | 12/2005 |
| 2010/0036375 A1 | 2/2010 | Regadas | | EP | 1632192 | 3/2006 |
| 2010/0042143 A1 | 2/2010 | Cunningham | | EP | 1642543 | 4/2006 |
| 2010/0049187 A1 | 2/2010 | Carlton et al. | | EP | 1645238 | 4/2006 |
| 2010/0057081 A1 | 3/2010 | Hanna | | EP | 1645240 | 4/2006 |
| 2010/0057082 A1 | 3/2010 | Hanna | | EP | 1649821 | 4/2006 |
| 2010/0057083 A1 | 3/2010 | Hanna | | EP | 1707143 | 10/2006 |
| 2010/0057084 A1 | 3/2010 | Hanna | | EP | 1769765 | 4/2007 |
| 2010/0063500 A1 | 3/2010 | Muszala | | EP | 1769766 | 4/2007 |
| 2010/0069903 A1 | 3/2010 | Allen, IV et al. | | EP | 1929970 | 6/2008 |
| 2010/0069904 A1 | 3/2010 | Cunningham | | EP | 1683496 | 12/2008 |
| 2010/0069953 A1 | 3/2010 | Cunningham et al. | | GB | 623316 | 5/1949 |
| 2010/0076427 A1 | 3/2010 | Heard | | GB | 1490585 | 11/1977 |
| 2010/0076430 A1 | 3/2010 | Romero | | GB | 2214430 A | 6/1989 |
| 2010/0076431 A1 | 3/2010 | Allen, IV | | GB | 2213416 A | 8/1989 |
| 2010/0076432 A1 | 3/2010 | Horner | | JP | 61-501068 | 9/1984 |
| 2010/0087816 A1 | 4/2010 | Roy | | JP | 6-502328 | 3/1992 |
| | | | | JP | 5-5106 | 1/1993 |

| | | |
|---|---|---|
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000-350732 | 12/2000 |
| JP | 2000342599 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 89/00757 | 1/1989 |
| WO | WO 92/04873 | 4/1992 |
| WO | WO 92/06642 | 4/1992 |
| WO | WO 93/21845 | 11/1993 |
| WO | WO 94/08524 | 4/1994 |
| WO | WO 94/20025 | 9/1994 |
| WO | WO 95/02369 | 1/1995 |
| WO | WO 95/07662 | 3/1995 |
| WO | WO 95/15124 | 6/1995 |
| WO | WO 96/05776 | 2/1996 |
| WO | WO 96/22056 | 7/1996 |
| WO | WO 96/13218 | 9/1996 |
| WO | WO 97/00646 | 1/1997 |
| WO | WO 97/00647 | 1/1997 |
| WO | WO 97/10764 | 3/1997 |
| WO | WO 97/24073 | 7/1997 |
| WO | WO 97/24993 | 7/1997 |
| WO | WO 98/27880 | 7/1998 |
| WO | WO 99/03407 | 1/1999 |
| WO | WO 99/03408 | 1/1999 |
| WO | WO 99/03409 | 1/1999 |
| WO | WO 99/12488 | 3/1999 |
| WO | WO 99/23933 | 5/1999 |
| WO | WO 99/40857 | 8/1999 |
| WO | WO 99/40861 | 8/1999 |
| WO | WO 99/51158 | 10/1999 |
| WO | WO 99/66850 | 12/1999 |
| WO | WO 00/24330 | 5/2000 |
| WO | WO 00/24331 | 5/2000 |
| WO | WO 00/36986 | 6/2000 |
| WO | WO 00/41638 | 7/2000 |
| WO | WO 00/47124 | 8/2000 |
| WO | WO 00/53112 | 9/2000 |
| WO | WO 01/17448 | 3/2001 |
| WO | WO 01/54604 | 8/2001 |
| WO | WO 02/07627 | 1/2002 |
| WO | WO 02/067798 | 9/2002 |
| WO | WO 02/080783 | 10/2002 |
| WO | WO 02/080784 | 10/2002 |

OTHER PUBLICATIONS

Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Carbonell et al., "Comparison of the Gyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectomy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques". OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.

Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Intl Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 dated Jun. 15, 2009.
Int'l Search Report EP 09 152898.4 dated Jun. 10, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.

* cited by examiner

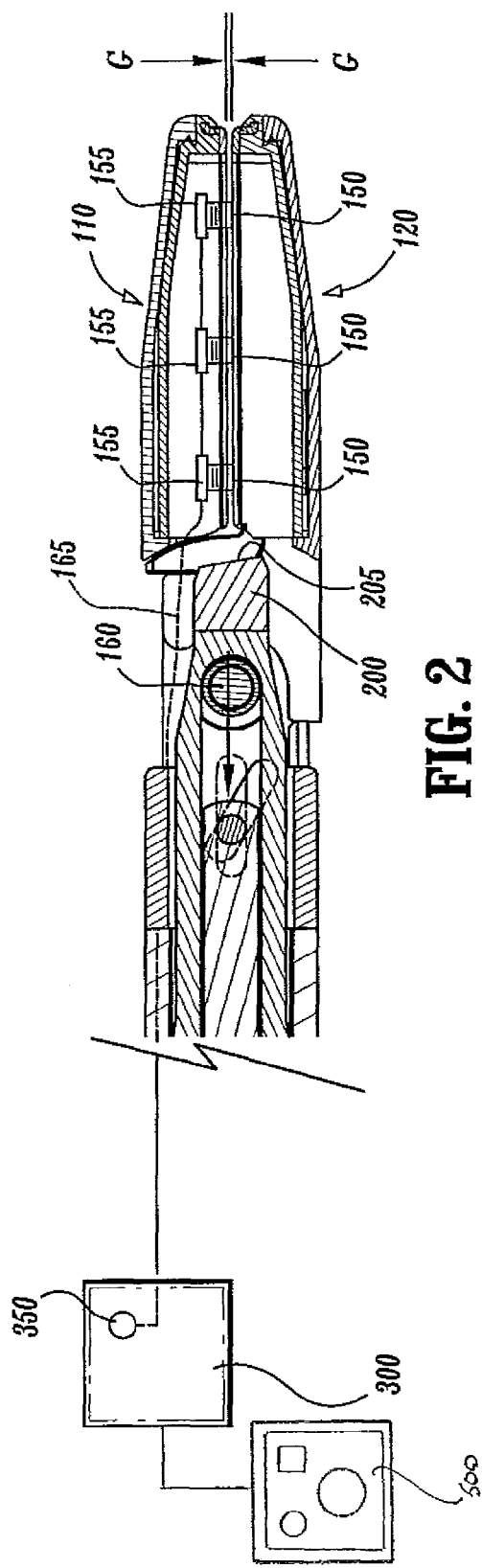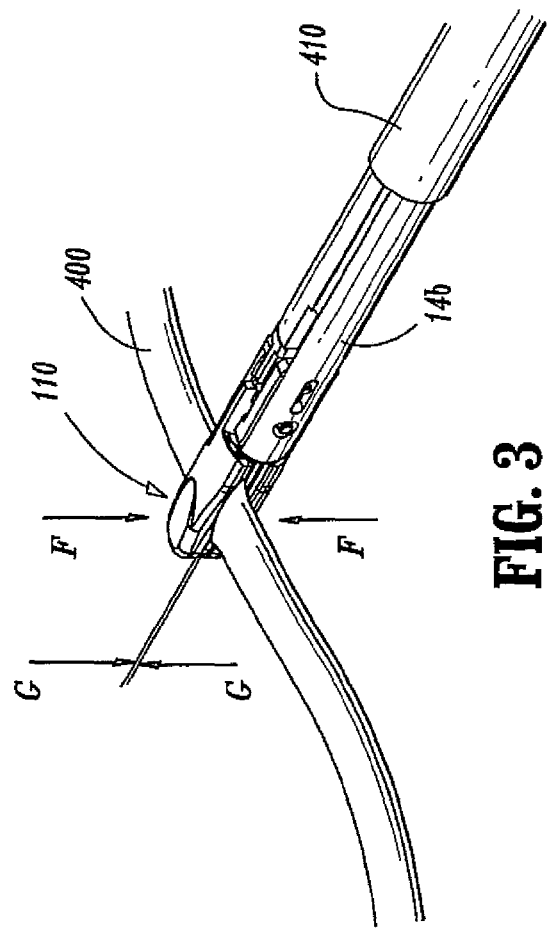
FIG. 2
FIG. 3

TISSUE SEALER WITH NON-CONDUCTIVE VARIABLE STOP MEMBERS AND METHOD OF SEALING TISSUE

CROSS-REFERENCE TO RELATED APPLICATION

The present application is a continuation application of U.S. Ser. No. 10/846,262 now U.S. Pat. No. 7,491,201 filed by Shields et al. on May 14, 2004, which claims the benefit of priority to U.S. Provisional Application Ser. No. 60/470,632 filed on May 15, 2003 by Shields et al., both of which are incorporated by reference herein.

BACKGROUND

The present disclosure relates to an electrosurgical instrument and method for performing electrosurgical procedures. More particularly, the present disclosure relates to an open or endoscopic bipolar electrosurgical forceps and method of using same which includes a selectively-variable, non-conductive stop member associated with one or both of the opposing jaw members. The selectively-variable, non-conductive stop member is designed to control the gap distance between opposing jaw members and enhance the manipulation and gripping of tissue during the sealing process.

TECHNICAL FIELD

Forceps utilize mechanical action to constrict, grasp, dissect and/or clamp tissue. Electrosurgical forceps utilize both mechanical clamping action and electrical energy to effect hemostasis by heating the tissue and blood vessels. By controlling the intensity, frequency and duration of the electrosurgical energy applied through the jaw members to the tissue, the surgeon can coagulate, cauterize and/or seal tissue.

In order to effect a proper seal with larger vessels or thick tissue, two predominant mechanical parameters must be accurately controlled: the pressure applied to the tissue; and the gap distance between the electrodes. As can be appreciated, both of these parameters are affected by the thickness of vessels or tissue. More particularly, accurate application of pressure is important for several reasons: to reduce the tissue impedance to a low enough value that allows enough electrosurgical energy through the tissue; to overcome the forces of expansion during tissue heating; and to contribute to the end tissue thickness which is an indication of a good seal. It has been determined that fused tissue is optimum between about 0.001 inches to about 0.006 inches for small vessels and tissues and about 0.004 inches to about 0.008 inches for large, soft tissue structures. Below these ranges, the seal may shred or tear and above this range the tissue may not be properly or effectively sealed.

It is thought that the process of coagulating or cauterizing small vessels is fundamentally different than electrosurgical vessel or tissue sealing. "Vessel sealing" or "tissue sealing" is defined as the process of liquefying the collagen, elastin and ground substances in the tissue so that it reforms into a fused mass with significantly-reduced demarcation between the opposing tissue structures. In contrast, the term "cauterization" is defined as the use of heat to destroy tissue (also called "diathermy" or "electrodiathermy") and the term "coagulation" is defined as a process of desiccating tissue wherein the tissue cells are ruptured and dried. Coagulation of small vessels is usually sufficient to permanently close them, however, larger vessels or tissue need to be "sealed" to assure permanent closure.

Numerous electrosurgical instruments have been proposed in the past for various open and endoscopic surgical procedures. However, most of these instruments cauterize or coagulate tissue and are normally not designed to provide uniformly reproducible pressure on the blood vessel or tissue which, if used for sealing purposes, would result in an ineffective or non-uniform seal. For example, U.S. Pat. No. 2,176,479 to Willis, U.S. Pat. Nos. 4,005,714 and 4,031,898 to Hiltebrandt, U.S. Pat. Nos. 5,827,274, 5,290,287 and 5,312,433 to Boebel et al., U.S. Pat. Nos. 4,370,980, 4,552,143, 5,026,370 and 5,116,332 to Lottick, U.S. Pat. No. 5,443,463 to Stern et al., U.S. Pat. No. 5,484,436 to Eggers et al. and U.S. Pat. No. 5,951,549 to Richardson et al., all relate to electrosurgical instruments for coagulating, cauterizing, and cutting vessels or tissue.

Many of these instruments include blade members or shearing members which simply cut tissue in a mechanical and/or electromechanical manner and are relatively ineffective for vessel or tissue sealing purposes. Other instruments generally rely on clamping pressure alone to procure proper sealing thickness and are often not designed to take into account gap tolerances and/or parallelism and flatness requirements which are parameters which, if properly controlled, can assure a consistent and effective tissue seal. For example, it is known that it is difficult to adequately control thickness of the resulting sealed tissue by controlling clamping pressure alone for either of two reasons: 1) if too much force is applied, there is a possibility that the two poles will touch and energy will not be transferred through the tissue resulting in an ineffective seal; or 2) if too low a force is applied, a thicker less reliable seal is created.

Thus, a need exists to develop an electrosurgical instrument which effectively and consistently seals tissue and solves the aforementioned problems. This instrument should be designed to regulate the gap distances between opposing jaws members to procure a consistent and effective seal. The instrument may also be designed to reduce the chances of the opposing jaws short circuiting during activation and assist in manipulating, gripping and holding the tissue prior to and during electrosurgical activation.

SUMMARY

According to one embodiment of the present disclosure, a bipolar forceps for sealing tissue is disclosed. The forceps includes an elongated shaft having opposing jaw members at a distal end thereof each of the jaw members including an electrically conductive sealing surface affixed thereto. The jaw members are movable relative to one another from a first position wherein the electrically conductive sealing surfaces are disposed in spaced relation relative to one another to a second position wherein the electrically conductive sealing surfaces are moved closer to one another for grasping tissue and maintained at a distance relative to one another. Each electrically conductive sealing surface is adapted to be connected to a source of electrical energy such that the electrically conductive sealing surfaces are capable of conducting energy through tissue grasped therebetween to effect a tissue seal. The distance between the electrically conductive sealing surfaces is selectively adjustable based upon a sensed pre-surgical condition during activation.

A method of sealing tissue is also contemplated by the present disclosure. The method includes an initial step of providing a bipolar forceps including a shaft having opposing jaw members at a distal end thereof which cooperate to grasp tissue therebetween, each of the jaw members including an electrically conductive sealing surface connected to a source of electrosurgical energy. The method also includes the steps of: adjusting a distance between the electrically conductive sealing surface based upon a sensed pre-surgical condition during activation, actuating the jaw members to grasp tissue between opposing jaw members, and conducting energy to the jaw members through tissue held therebetween to effect a tissue seal.

Another method of sealing tissue is also contemplated by the present disclosure. The method includes an initial step of providing a bipolar forceps including a shaft having opposing jaw members at a distal end thereof which cooperate to grasp tissue therebetween, each of the jaw members including an electrically conductive sealing surface connected to a source of electrosurgical energy. The method also includes the steps of actuating the jaw members to grasp tissue between opposing jaw members, conducting energy to the jaw members through tissue held therebetween to effect a tissue seal and adjusting a distance between the electrically conductive sealing surface based upon a sensed surgical condition during activation.

A further method of sealing tissue is contemplated by the present disclosure. The method includes an initial step of providing a bipolar forceps which includes a shaft having opposing jaw members at a distal end thereof each of the jaw members including an electrically conductive sealing surface, at least one of the electrically conductive sealing surfaces connected to a source of electrosurgical energy. The method also includes the steps of: actuating the jaw members to grasp tissue between opposing jaw members, wherein the jaw members are disposed at a distance relative to one another, adjusting the distance between the jaw members during the conducting step based upon a sensed surgical condition during activation and conducting energy to the jaw members through tissue held therebetween.

BRIEF DESCRIPTION OF THE DRAWINGS

Various embodiments of the present disclosure are described herein with reference to the drawings wherein:

FIG. 2 is a side, partial internal view of an end effector assembly shown in closed configuration;

FIG. 3 is a rear, perspective view of the end effector of FIG. 2 shown with tissue grasped therein.

DETAILED DESCRIPTION

Figure 1A:
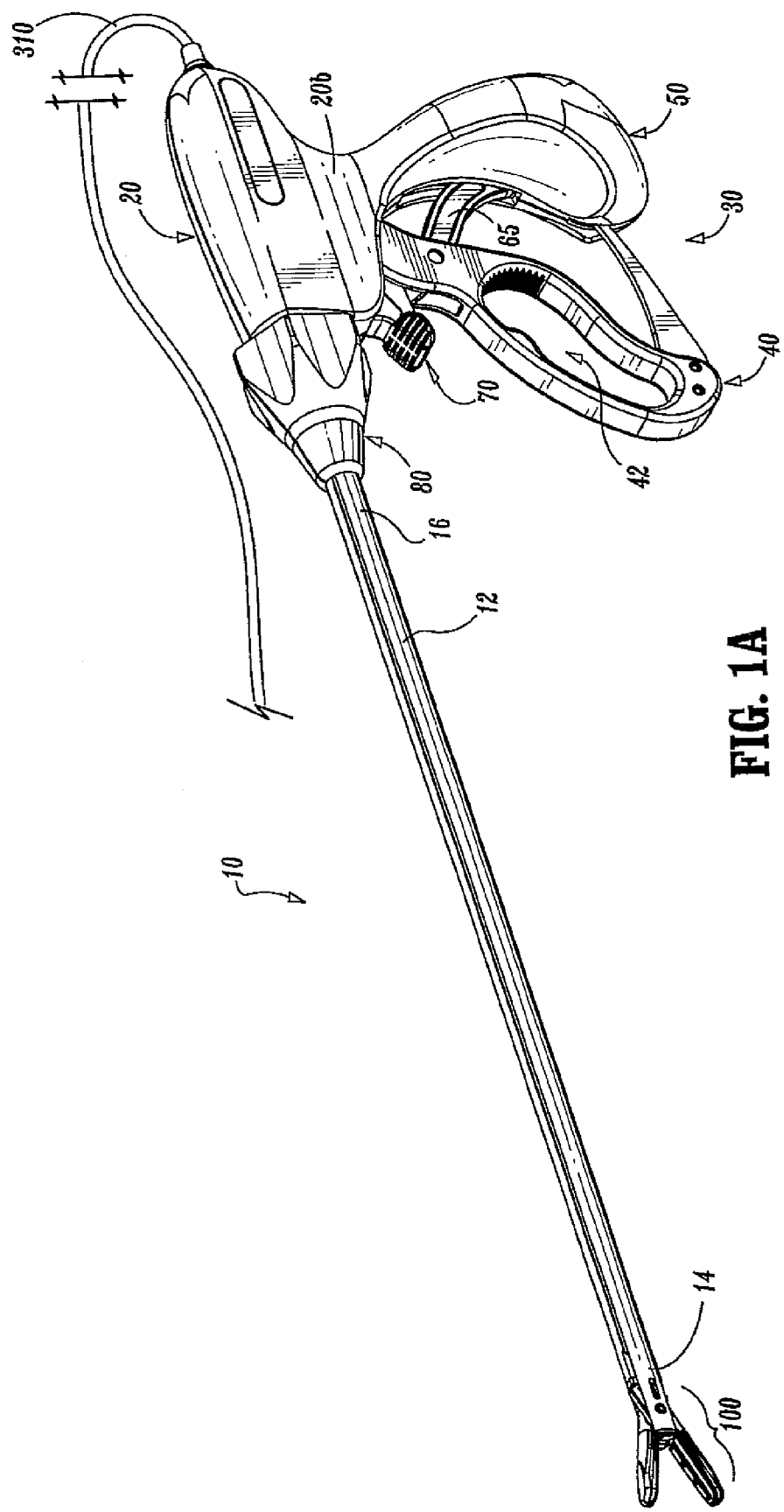
FIG. 1A is a perspective view of an endoscopic bipolar forceps which is configured to support a variable stop member assembly according to the present disclosure.

Referring now to FIGS. 1A-4, an endoscopic bipolar forceps 10 is shown by way of example for use with various endoscopic surgical procedures. Either an endoscopic instrument or an open instrument may be utilized for supporting the variable stop member assembly according to the present disclosure. Obviously, different electrical and mechanical connections and considerations apply to each particular type of instrument, however, the novel aspects with respect to the stop member assembly and its operating characteristics remain generally consistent with respect to both the open or endoscopic designs. Forceps 10 is shown by way of example and other electrosurgical forceps are also envisioned which may support the stop member assembly of the present disclosure. In the drawings and in the description which follows, the term "proximal", as is traditional, will refer to the end of the forceps 10 which is closer to the user, while the term "distal" will refer to the end of the forceps which is further from the user.

Figure 1B:
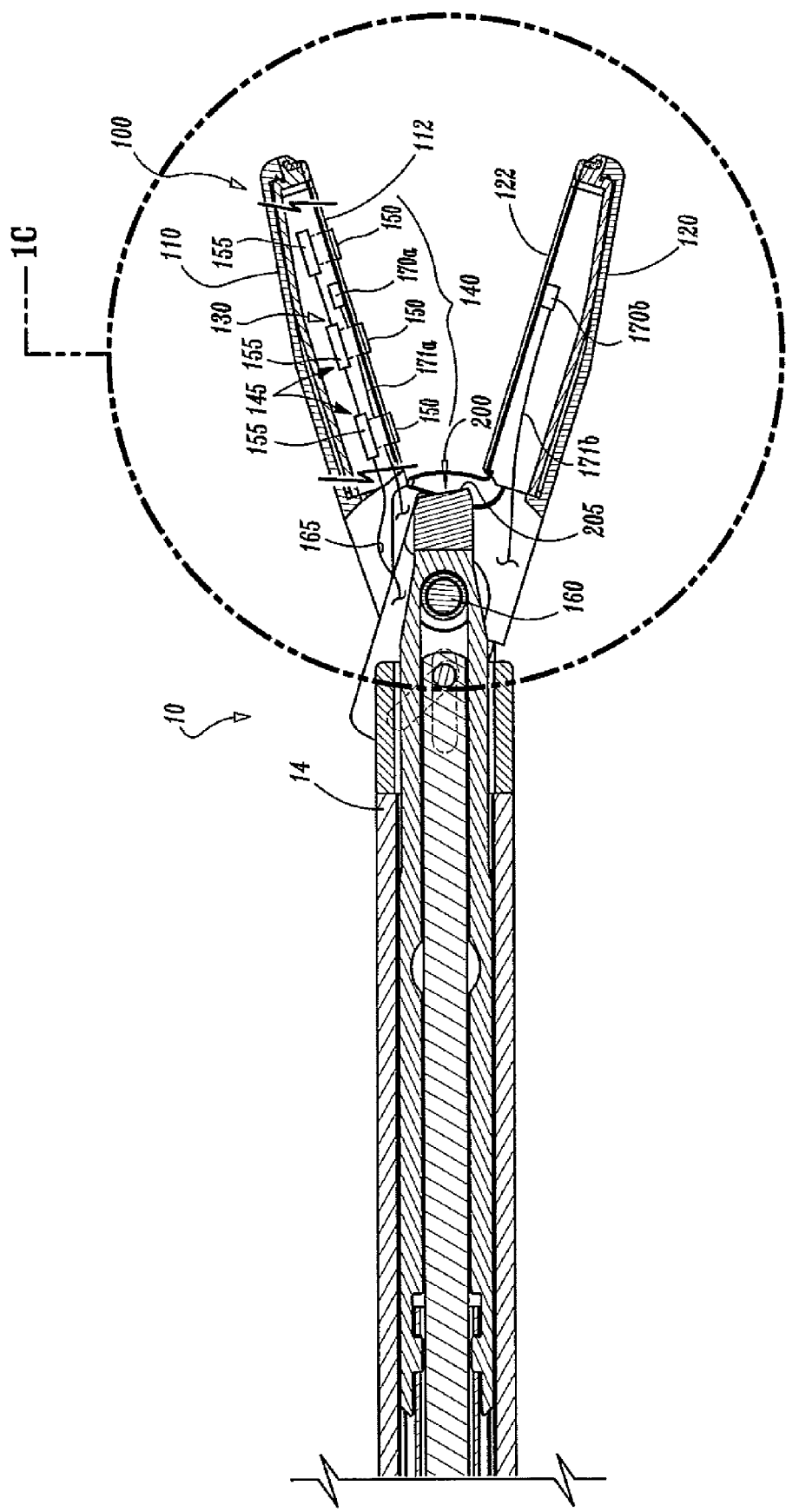
FIG. 1B is a side, partial internal view of an endoscopic forceps showing a selectively adjustable stop member assembly according to the present disclosure.
Figure 1C:
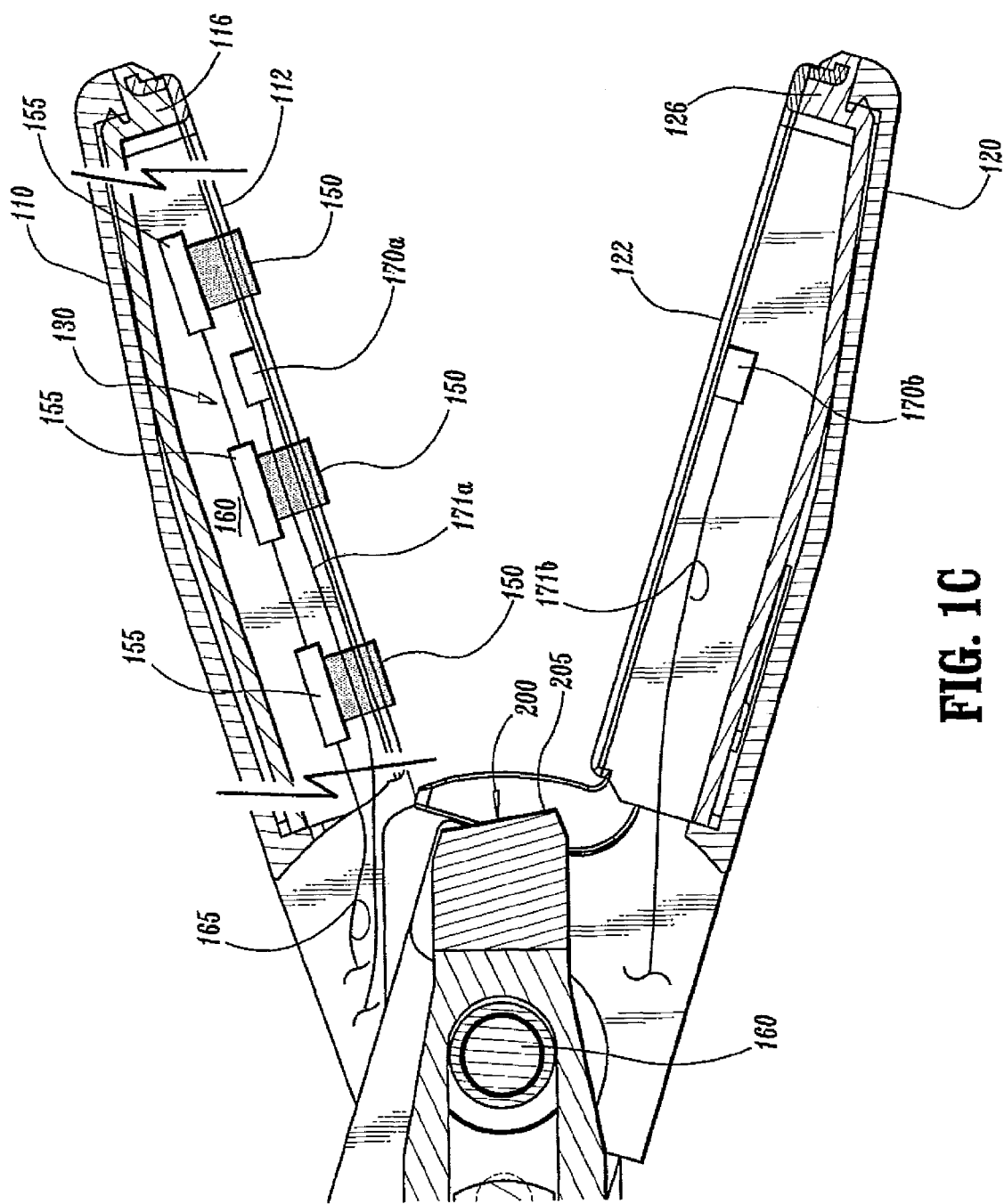
FIG. 1C is an enlarged view of the area of detail of FIG. 1B.

FIGS. 1A-1C show an endoscopic vessel sealing forceps 10 which is configured to support an electrode sealing assembly 100. More particularly, forceps 10 generally includes a housing 20, a handle assembly 30, a rotating assembly 80, a trigger assembly 70 and the end effector assembly 100 which mutually cooperate to grasp, seal and, if warranted, divide tissue. The forceps 10 includes a shaft 12 which has a distal end 14 dimensioned to mechanically engage the end effector assembly 100 and a proximal end 16 which mechanically engages the housing 20 proximate the rotating assembly 80.

Forceps 10 also includes a plug (not shown) which connects the forceps 10 to a source of electrosurgical energy, e.g., an electrosurgical generator 500, via an electrical cable 310. Handle assembly 30 includes a fixed handle 50 and a movable handle 40. Handle 40 moves relative to fixed handle 50 to actuate the end effector assembly 100 and enable a user to grasp and manipulate tissue 400 (See FIG. 3). The end effector assembly 100 includes a pair of opposing jaw members 110 and 120 which each have an electrically conductive sealing surface 112 and 122, respectively, attached thereto for conducting electrosurgical energy through tissue 400 held therebetween. More particularly, the jaw members 110 and 120 move in response to movement of the handle 40 from an open position wherein the electrically conductive sealing surfaces 112 and 122 are disposed in spaced relation relative to one another, to a clamping or closed position wherein the electrically conductive sealing surfaces 112 and 122 cooperate to grasp tissue therebetween.

The housing 20 encloses a drive assembly (not shown) which cooperates with the movable handle 40 to impart movement of the jaw members 110 and 120 from the open position to the clamping or closed position. One Example of a handle assembly is shown and described in commonly-owned U.S. application Ser. No. 10/389,894 entitled "VESSEL SEALER AND DIVIDER AND METHOD MANUFACTURING SAME" which is hereby incorporated by reference herein in its entirety. The handle assembly of this particular disclosure is generally be characterized as a four-bar mechanical linkage which provides a unique mechanical advantage when sealing tissue between the jaw members 110 and 120. For example, once the desired position for the sealing site is determined and the jaw members 110 and 120 are properly positioned, handle 40 may be compressed fully to lock the electrically conductive sealing surfaces 112 and 122 in a closed position against the tissue. The details relating to the inter-cooperative relationships of the inner-working components of forceps 10 are disclosed in the above-cited commonly-owned U.S. patent application Ser. No. 10/369,894. When the electrically conductive sealing surfaces 112 and 122 of the jaw members 110 and 120 are fully compressed about the tissue 400, the forceps 10 is now ready for selective application of electrosurgical energy (See FIG. 3). Another example of an endoscopic handle assembly is disclosed in U.S. patent application Ser. No. 10/460,926 entitled "VESSEL SEALER AND DIVIDER FOR USE WITH SMALL TROCARS AND CANNULAS", the entire contents of this application being incorporated by reference herein.

Experimental results suggest that the magnitude of pressure exerted on the tissue 400 by the electrically conductive sealing surfaces 112 and 122 is important in assuring a proper surgical seal. Pressures within a working range of about 3 kg/cm² to about 16 kg/cm² and, in embodiments, within a working range of about 7 kg/cm² to about 13 kg/cm² have been shown to be effective for sealing various small tissue types. Pressure within a working range of about 4.5 kg/cm² to about 8.5 kg/cm² are optimal for large soft tissue structures.

As explained above, movement of the handle assembly 30, e.g., via a four-bar linkage, ultimately causes the opposing jaw members 110 and 120 to move relative to one another. As can be appreciated, the significant mechanical advantage associated with the four-bar linkage permits facile, consistent and uniform compression of the jaw members 110 and 120 about the tissue 400. Other details and advantages of the four-bar mechanical linkage are more fully discussed with respect to the above-mentioned commonly-owned U.S. patent application Ser. No. 10/369,894.

As best seen in FIGS. 1A-1C, forceps 10 also includes a trigger 70 which advances a knife 200 disposed within the end effector assembly 100. Once a tissue seal is formed, the user can activate the trigger 70 to separate the tissue 400 along the tissue seal. Knife 200 includes a sharpened edge 205 for severing the tissue 400 held between the jaw members 110 and 120 at the tissue sealing site.

A rotating assembly 80 may also be incorporated with forceps 10. In embodiments, rotating assembly 80 is mechanically associated with the shaft 12 and the drive assembly (not shown). Movement of the rotating assembly 80 imparts similar rotational movement to the shaft 12 which, in turn, rotates the end effector assembly 100. These features along with the unique electrical configuration for the transference of electrosurgical energy through the handle assembly 20 and the rotating assembly 80 are described in more detail in the above-mentioned commonly-owned U.S. patent application Ser. Nos. 10/369,894 and 10/460,926.

As best seen with respect to FIGS. 1A-2, end effector assembly 100 attaches to the distal end 14 of shaft 12. The jaw members 110 and 120 are pivotable about a pivot 160 from the open to closed positions upon relative reciprocation, i.e., longitudinal movement, of the drive assembly (not shown). Again, mechanical and cooperative relationships with respect to the various moving elements of the end effector assembly 100 are further described by example with respect to the above-mentioned commonly-owned U.S. patent application Ser. Nos. 10/369,894 and 10/460,926.

It is envisioned that the forceps 10 may be designed such that it is fully or partially disposable depending upon a particular purpose or to achieve a particular result. For example, end effector assembly 100 may be selectively and releasably engageable with the distal end 14 of the shaft 12 and/or the proximal end 16 of the shaft 12 may be selectively and releasably engageable with the housing 20 and handle assembly 30. In either of these two instances, the forceps 10 would be considered "partially disposable" or "reposable", i.e., a new or different end effector assembly 100 (or end effector assembly 100 and shaft 12) selectively replaces the old end effector assembly 100 as needed.

Each of the jaw members 110 and 120 includes an electrically conductive sealing surface 112 and 122, respectively disposed on an inner-facing surface thereof. It is envisioned that the electrically conductive surfaces 112 and 122 cooperate to seal tissue 400 held therebetween upon the application of electrosurgical energy. Insulators 116 and 126 (together with the outer, non-conductive surfaces of the jaw members 110 and 120) may be included to limit and/or reduce many of the known undesirable effects related to tissue sealing, e.g., flashover, thermal spread and stray current dissipation (See FIG. 1C).

In embodiments, a least one of the electrically conductive surfaces, e.g., 112, of one of the jaw members, e.g., 110, includes a longitudinally-oriented channel 210 defined therein (See FIG. 4) which extends from the proximal end of the electrically conductive sealing surface 112 to the distal end. The channel 210 facilitates longitudinal reciprocation of the knife 200 along a desired cutting plane to effectively and accurately separate the tissue 400 along a formed tissue seal.

By controlling the intensity, frequency and duration of the electrosurgical energy applied to the tissue 400, the user can selectively seal tissue 400. As mentioned above, two mechanical factors play an important role in determining the resulting thickness of the sealed tissue and effectiveness of the seal, i.e., the pressure applied between opposing jaw members 110 and 120 and the gap distance "G" between the opposing sealing surfaces 112 and 122 of the jaw members 110 and 120, respectively, during the sealing process.

However, thickness of the resulting tissue seal cannot be adequately controlled by force alone. In other words, too much force and the two jaw members 110 and 120 would touch and possibly short resulting in little energy traveling through the tissue 400 thus resulting in a bad tissue seal. Too little force and the seal would be too thick. Applying the correct force is also important for other reasons: to reduce the tissue impedance to a low enough value that allows enough current through the tissue 400; and to overcome the forces of expansion during tissue heating in addition to contributing towards creating the required end tissue thickness which is an indication of a good seal.

In order to achieve a desired spacing between the electrically conductive surfaces 112 and 122 of the respective jaw members 110 and 120, (i.e., gap distance "G") and apply a desired force to seal the tissue 400, at least one jaw member 110 and/or 120 includes at least one stop member, e.g., 150, to limit the movement of the two opposing jaw members 110 and 120 relative to one another. In one embodiment, the stop member, e.g., 150, extends from at least one of the sealing surfaces 112, 122 a predetermined distance according to the specific material properties of the stop member 150 (e.g., compressive strength, thermal expansion, etc.) to yield a consistent and accurate gap distance "G" during sealing. In one embodiment, the gap distance "G" between opposing sealing surfaces 112 and 122 during sealing ranges from about 0.001 inches to about 0.008 inches. For smaller tissue types the gap distance may be between about 0.002 inches to about 0.003 inches and for larger tissue types the gap distance may be between about 0.004 inches to about 0.007 inches.

In embodiments, stop members 150 are made from an insulative material, e.g., parylene, nylon and/or ceramic and are dimensioned to limit opposing movement of the electrically conductive sealing surfaces 112 and 122 to within the above mentioned gap range "G". It is envisioned that the stop members 150 may be disposed on one or both of the electrically conductive sealing surfaces 112 and 122 depending upon a particular purpose or to achieve a particular result.

As best shown in FIGS. 1B and 1C, at least of the jaw members includes a selectively adjustable stop member assembly 140 which allows a surgeon to regulate the gap distance "G" depending upon a particular tissue type and/or tissue thickness. More particularly, at least one of the jaw members, e.g., jaw member 110, includes a cavity 130 disposed therein which is dimensioned to house the stop member assembly 140. Stop member assembly 140 includes a plurality of selectively adjustable stop member control units 145 which includes a stop member 150 and a controller 155. More particularly, the controller 155 is designed to receive signals from a control source 300 (FIG. 2) which may be attached to an electrosurgical generator 500 or incorporated into the housing of the forceps 10. The control source 300 signals the controller 155 to electrically, mechanically or electro-mechanically adjust the distance the stop member(s) 150 projects or extends from the electrically conductive sealing surface 112 (and/or 122). The distance that the stop member(s) 150 projects from the electrically conductive sealing surface 112 (and/or 122) determines the ultimate gap distance "G" (See FIG. 2).

It is envisioned that the controller 155 may adjust the distance that each stop member 150 extends from the sealing surface 112 is any known fashion. For example, each stop member 150 and its corresponding controller 155 may be threadably connected such that the controller 155 "unscrews" the stop member 150 to adjust the distance that the stop member 150 extends from the sealing surface 112. Thus, by controlling the amount that the stop member 150 unscrews from the controller 155, a surgeon can selectively regulate (or a control source 300 may automatically regulate) the gap distance "G". Other mechanical systems (not shown) are also envisioned to allow selective regulation of the gap distance "G", e.g., gearing mechanisms, camming mechanisms, pneumatic mechanisms, hydraulic mechanisms, etc. Electromechanical systems are also contemplated, e.g., electro-mechanical actuators, ferroelectric actuators, piezo-electric actuators, piezo-ceramic actuators, magnetostrictors and rotational actuators, etc.

It is envisioned that the controller 155 may cooperate with a sensor assembly 170a and 170b (or a plurality of sensors) which determines or measures tissue thickness, tissue moisture, tissue type, tissue impedance, etc. and automatically signals the control source 300 to signal the controller 155 to adjust the stop members 150 to extend a specific distance (i.e., a "desired" gap distance "G") from the electrically conductive sealing surface 112 prior to activation. The desired gap distance "G" (which directly corresponds to the specified distance that the stop members 150 extend from the electrically conductive sealing surface 112) may be selected from a look-up table or determined by a computer algorithm stored within the control source 300. It is envisioned that the stop members are selectively adjustable to protrude about 0.001 inches to about 0.008 inches from the electrically conductive sealing surfaces 112 (and/or 122) of the jaw members 110 (and/or 120).

It is also contemplated that one or more stop members 150 may be individually controllable (via controller 155 or manually) to vary the gap distance along or across the sealing surfaces depending upon a particular purpose or to achieve a particular tissue seal. Moreover, it is envisioned that varying the distance that stop member(s) project from the sealing surface(s) may produce different results for different tissue types and may prove desirable for one or more particular tissue types or one or more different surgical procedures.

The sensors 170a and 170b are connected to the control source 300 (or electrosurgical generator) via cables 171a and 171b, respectively. The sensors 170a and 170b may form a part of a closed-loop control system which automatically adjusts the forceps 10 prior to and/or during activation based on pre-surgical parameters and continually-sensed parameters. For example, the stop members 150 may be adjusted based upon a pre-surgical parameter such as tissue thickness, tissue type, tissue compliance, tissue impedance, etc. One example of a closed-loop control system is described in commonly-owned U.S. patent application Ser. No. 10/427,832 filed on May 1, 2003 entitled "METHOD AND SYSTEM FOR CONTROLLING OUTPUT OF RF MEDICAL GENERATOR" the entire contents of which are hereby incorporated by reference herein. For example, the stop member(s) 150 may be set according to a pre-surgical condition (either automatically based upon a sensed condition (e.g., tissue impedance, tissue type, tissue clarity, tissue compliance, etc.)) or manually by the surgeon.

It is also envisioned that the stop member(s) 150 may be adjusted during activation based upon a continually-sensed surgical condition (e.g., tissue impedance, tissue type, tissue clarity, tissue compliance, etc.) utilizing a feed back control loop. It is envisioned that this may allow the control system to achieve a "slow close" condition. More particularly, one technique for sealing larger tissue structures (e.g., lung, liver, bronchus, etc.) is a so-called "slow-close" surgical technique which involves activating the surgical instrument prior to obtaining a fully ratcheted position. As can be appreciated, this type of procedure is very difficult to master manually due to the many variables involved with the sealing process and, as a result, the instrument may short or the sealing cycle may complete prior to obtaining the fully closed ratcheted position. It is envisioned that the automatic stop member adjustment system described above may enable slow close activation which may lead to more effective sealing of large tissue structures. For example, the surgeon can grasp the tissue in a customary manner and fully ratchet the forceps about the tissue within the desired pressure ranges. The stop member(s) 150 can be programmed to activate in a "slow close" manner and automatically adjust from a large gap distance e.g., about 0.10 inches to within a gap range of about 0.001 inches to about 0.008 inches during activation. The stop member control assembly 140 may also be coupled to a feedback control system which automatically regulates the "slow close" technique based upon tissue thickness, tissue temperature, tissue impedance, tissue moisture, tissue clarity, tissue compliance during activation. As can be appreciated, this enables any surgeon to perform a slow close technique for sealing lager tissue structures.

A control knob 350 (See FIG. 2) may also be included to permit a surgeon to manually adjust the distance that the stop members 150 protrude from the electrically conductive sealing surface 112 (and/or 122) depending upon a particular purpose.

Figure 4:
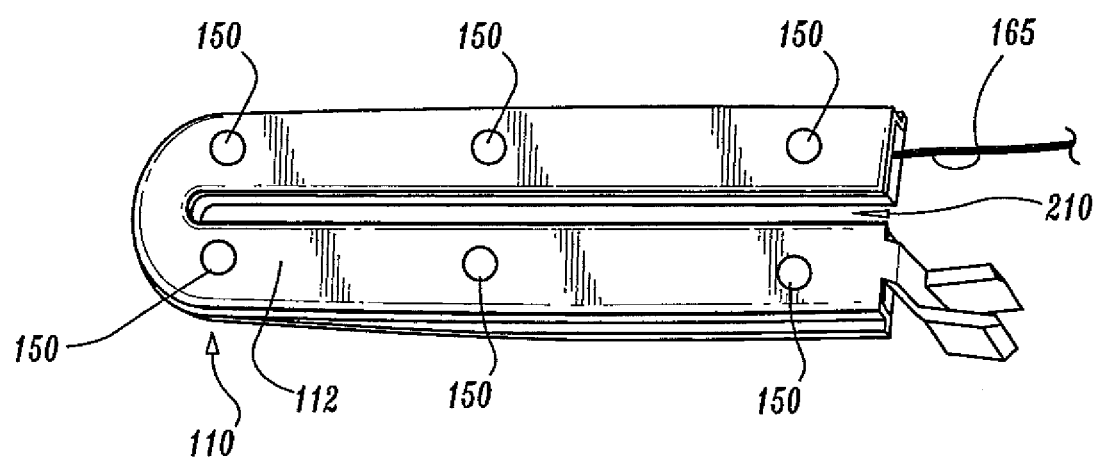
FIG. 4 is an enlarged, perspective view of an electrically conductive sealing surface of the end effector assembly showing a series of selectively adjustable stop members disposed thereon.

FIG. 4 shows one contemplated configuration of the stop members 150 disposed on or protruding from the electrically conductive sealing surface 112. It is envisioned that the stop members 150 can be positioned on either or both jaw members 110 and 120 depending upon a particular purpose or to achieve a desired result. More particularly and as illustrated in FIG. 4, a series of longitudinally-oriented tab-like stop members 150 are disposed along either side of the knife channel 210 of jaw member 110. In embodiments, the stop members 150 may be configured in any known geometric or polynomial configuration, e.g., triangular, rectilinear, circular, ovoid, scalloped, etc., depending upon a particular purpose. Moreover, it is contemplated that any combination of different stop members 150 may be assembled along the sealing surfaces 112 (and/or 122) to achieve a desired gap distance "G". A ceramic or insulative coating may be deposited or sprayed onto the tissue engaging surface of the stop members 150. Thermal spraying techniques are contemplated which involve depositing a broad range of heat resistant and insulative materials on the tissue engaging surfaces of the stop members 150, high velocity Oxy-fuel deposition, plasma deposition, etc.

Further, although it is the stop members 150 may be selectively adjustable to protrude about 0.001 inches to about 0.008 inches from the electrically conductive sealing surfaces 112, in some cases the stop members 150 may protrude more or less depending upon a particular purpose. For example, it is contemplated that the type of material used for the stop members 150 and that material's ability to absorb the desired range of compressive closure forces between jaw members 110 and 120 will vary and, therefore, the overall distance that the stop members 150 may have to extend from the electrically conducive sealing surfaces 112 may have to adjusted to compensate for the particular stop member 150 material being utilized to produce the desired gap distance "G".

In other words, the compressive strength of the stop member material along with the desired or ultimate gap distance "G" required for effective sealing are parameters which should be considered during activation since one material may have to be adjusted differently from another material to achieve the same gap distance "G". For example, the compressive strength of nylon is different from ceramic and, therefore, the nylon material may have to extend a greater distance from the electrically conductive sealing surface 112 to counteract the closing force of the opposing jaw members 110 and 120 and to achieve the same desired gap distance "G". As can be appreciated, these considerations may be automatically regulated or controlled at the control source 300 via a computer algorithm or look up table.

The present disclosure also relates to a method of sealing tissue utilizing a selectively adjustable stop member 150 and includes the steps of: providing a bipolar forceps 10 having a shaft 12 and opposing jaw members 110 and 120 which cooperate to grasp tissue 400 therebetween; at least one selectively extendible and non-conductive stop member 150 disposed on an electrically conductive surface 112 of at least one of the jaw members, e.g., 110, which regulates the distance between the jaw members 110 and 120 when tissue 400 is held therebetween. The method further includes the steps of: connecting the electrically conductive sealing surfaces 112 and 122 of the jaw members 110 and 120 to a source of electrosurgical energy; adjusting the distance that the stop members 150 extend from the electrically conductive sealing surface 112 depending upon a pre-surgical condition or parameter; actuating the jaw members 110 and 120 to grasp tissue 400 between opposing electrically conductive sealing surfaces 112 and 122; conducting energy to the electrically conductive sealing surfaces 112 and 122 through tissue 400 held therebetween to effect a seal.

The adjusting step of the method may further include the steps of: sensing a pre-surgical condition or parameter such as tissue type, tissue thickness, tissue compliance, tissue impedance, etc. and signaling the controller 155 (via the control source 300 or directly) to selectively extend or retract the stop members 150 relative to the electrically conductive sealing surface 112 depending upon the sensed pre-surgical condition or parameter.

At least one of the jaw members, e.g., 110, of the providing step includes may include an electrically conductive sealing surface 112 having a longitudinally-oriented channel 210 defined therein which facilitates actuation of a knife 200 in a longitudinally reciprocating fashion within the channel 210 for severing the tissue 400 proximate the tissue sealing site. As can be appreciated, the method may also include the step of severing the tissue 400 along the tissue seal.

From the foregoing and with reference to the various figure drawings, those skilled in the art will appreciate that certain modifications can also be made to the present disclosure without departing from the scope of the same. For example, it may be desirable to add other features to the forceps 10, e.g., an articulating assembly to axially displace the end effector assembly 100 relative to the elongated shaft 12.

Moreover, it is contemplated that the presently disclosed forceps may include a disposable end effector assembly 100 which is selectively engageable with at least one portion of the electrosurgical instrument, e.g., shaft 12 and/or handle assembly 80. In one embodiment, the electrically conductive sealing surfaces 112 and 122 of the jaw members 110 and 120 are relatively flat to avoid current concentrations at sharp edges and to avoid arcing between high points. In addition and due to the reaction force of the tissue 400 when engaged, jaw members 110 and 120 may be manufactured to resist bending. For example, the jaw members 110 and 120 may be tapered along their respective widths which is advantageous for two reasons: 1) the taper will apply constant pressure for a constant tissue thickness at parallel; 2) the thicker proximal portion of the jaw members 110 and 120 will resist bending due to the reaction force of the tissue 400.

It is also contemplated that one or more stop members may be disposed adjacent to one or both electrically conductive sealing surfaces to regulate the gap distance between conductive surfaces. Alternatively, one or more selectively extendible stop members may be disposed on one or both electrically conductive sealing surface(s) and one or more stop members may be disposed adjacent to at least one of the electrically conductive surfaces. As can be appreciated, both sets of selectively adjustable stop members would cooperate with the controller (or manually) to adjust and regulate the gap distance.

The stop member(s) may be dimensioned in any known geometric configuration and may be disposed on or adjacent to one or both of the electrically conductive tissue sealing surfaces or operatively associated with one or both jaw members. Moreover, the controller and stop member may be integrally associated with one another or may be formed from two or more components so long as the stop member is selectively adjustable to regulate the distance between the jaw members prior to and/or during electrical activation.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A bipolar forceps for sealing tissue, comprising:
    an elongated shaft having opposing jaw members at a distal end thereof, each of the jaw members including an electrically conductive sealing surface affixed thereto, at least one of the jaw members movable relative to the other jaw member from a first position wherein the electrically conductive sealing surfaces are disposed in spaced relation relative to one another to a second position wherein the electrically conductive sealing surfaces are moved closer to one another for grasping tissue;
    each electrically conductive sealing surface adapted to connect to a source of electrical energy such that the electrically conductive sealing surfaces are capable of conducting energy through tissue grasped therebetween to effect a tissue seal, wherein the distance between the electrically conductive sealing surfaces is automatically adjustable in response to a sensed pre-surgical condition during activation.

2. A bipolar forceps for sealing tissue according to claim 1, further including at least one controller engagable with at least one of the electrically conductive sealing surfaces, the controller configured to control the distance between the electrically conductive sealing surfaces in response to a signal from a control source.

3. A bipolar forceps for sealing tissue according to claim 2, wherein the bipolar forceps includes at least one sensor disposed on at least one of the jaw members, the at least one sensor configured to sense the sensed pre-surgical condition selected from the group consisting of tissue impedance, tissue thickness, tissue compliance, and tissue type, and further configured to relay the sensed information to a control source which, in turn, is configured to send a signal to the controller.

4. A bipolar forceps for sealing tissue according to claim 1, wherein the forceps includes a selectively extendible knife for severing tissue along the tissue seal.

5. A bipolar forceps for sealing tissue according to claim 1, wherein the electrically conductive sealing surfaces are adjusted a distance in the range of about 0.001 inches to about 0.008 inches relative to one another.

6. A method of sealing tissue comprising the steps of
providing a bipolar forceps including a shaft having opposing jaw members at a distal end thereof which cooperate to grasp tissue therebetween, each of the jaw members including an electrically conductive sealing surface connected to a source of electrosurgical energy;
automatically adjusting a distance between the electrically conductive sealing surface in response to a sensed pre-surgical condition during activation;
actuating the jaw members to grasp tissue between opposing jaw members; and
conducting energy to the jaw members through tissue grasped therebetween to effect a tissue seal.

7. A method of sealing tissue according to claim 6, wherein the adjusting step further includes the steps of
sensing the sensed pre-surgical condition; and
signaling a controller to selectively adjust the distance between the electrically conductive sealing surfaces depending upon the sensed pre-surgical condition.

8. A method of sealing tissue according to claim 6, further comprising the step of severing the tissue along the tissue seal.

9. A method of sealing tissue according to claim 6, wherein after the conducting step, the method further includes the steps of:
sensing a tissue parameter during electrosurgical activation; and
signaling a controller to selectively adjust the distance between the electrically conductive sealing surfaces based upon the sensed tissue parameter.

10. A method of sealing tissue according to claim 9, wherein after the sensed signaling step, the method further includes the step of repeating the sensing and signaling steps until a desired seal is effected.

11. A method of sealing tissue comprising the steps of:
providing a bipolar forceps including a shaft having opposing jaw members at a distal end thereof which cooperate to grasp tissue therebetween, each of the jaw members including an electrically conductive sealing surface connected to a source of electrosurgical energy;
actuating the jaw members to grasp tissue between opposing jaw members, wherein the jaw members are disposed at a distance relative to one another;
automatically adjusting the distance between the electrically conductive sealing surfaces in response to a sensed surgical condition during activation; and
conducting energy to the jaw members through tissue grasped therebetween to effect a tissue seal.

12. A method of sealing tissue according to claim 11, wherein the adjusting step further includes the step of communicating with a feedback control system that continually senses surgical conditions during activation to automatically regulate the distance between the electrically conductive sealing surfaces.

13. A method of sealing tissue according to claim 11, wherein the adjusting step, further includes the step of communicating with a feedback control system to automatically regulate the distance between the electrically conductive sealing surfaces based upon at least one of tissue impedance, tissue temperature, tissue thickness, tissue moisture, tissue compliance or tissue clarity during activation.

14. A method of sealing tissue according to claim 11, wherein the step of adjusting includes adjusting the distance between the electrically conductive sealing surfaces so that the distance between the electrically conductive sealing surfaces becomes increasingly smaller.

* * * * *